United States Patent
Viole et al.

(10) Patent No.: US 7,048,680 B2
(45) Date of Patent: May 23, 2006

(54) MULTILUMEN CATHETER FOR MINIMIZING LIMB ISCHEMIA

(75) Inventors: Anthony Viole, Foothill Ranch, CA (US); Laksen Sirimanne, Tustin, CA (US); Steven F. Bolling, Ann Arbor, MI (US); Shawn O'Leary, Mission Viejo, CA (US); Wolfgang Werner, Carlsbad, CA (US)

(73) Assignee: Orqis Medical Corporation, Lake Forest, CA (US)

( * ) Notice: Subject to any disclaimer, the term of this patent is extended or adjusted under 35 U.S.C. 154(b) by 365 days.

(21) Appl. No.: 09/876,281

(22) Filed: Jun. 6, 2001

(65) Prior Publication Data

US 2002/0188166 A1 Dec. 12, 2002

(51) Int. Cl.
*A61N 1/362* (2006.01)

(52) U.S. Cl. .......................................... 600/16; 604/43
(58) Field of Classification Search ................... 604/43, 604/44, 6.16, 6.11, 500, 523, 532, 530, 529, 604/95.04; 600/16, 18

See application file for complete search history.

(56) References Cited

U.S. PATENT DOCUMENTS

| | | | | |
|---|---|---|---|---|
| 4,134,402 A | * | 1/1979 | Mahurkar | 128/214 |
| 4,405,313 A | | 9/1983 | Sisley et al. | 604/43 |
| 4,540,402 A | * | 9/1985 | Aigner | 604/44 |

(Continued)

FOREIGN PATENT DOCUMENTS

| | | | | |
|---|---|---|---|---|
| EP | 0 533 432 A1 | 3/1993 | | |
| EP | 0 711 574 A1 | 5/1996 | | 600/4.01 |
| WO | WO 99/19010 | 4/1999 | | |
| WO | WO 99/42156 | 8/1999 | | 600/4.01 |
| WO | WO 99/59652 | 11/1999 | | 600/16 |
| WO | WO 00/61207 | 10/2000 | | |

OTHER PUBLICATIONS

PCT International Search Report, App. No.: PCT/US 01/42774, App. Date: Oct. 15, 2001, 6 pages.
International Search Report, dated Jun. 15, 2003.
International Search Report dated Nov. 20, 2003; PCT/US 03/04401; filed Feb. 13, 2003.

*Primary Examiner*—Mark Bockelman
(74) *Attorney, Agent, or Firm*—Knobbe, Martens, Olson & Bear LLP

(57) ABSTRACT

A multilumen catheter that maximizes the blood flow into and out of the patient's vasculature while also providing for passive and/or active perfusion of tissue downstream of where the catheter resides in the vasculature. The inventive catheter comprises a proximal end, a first distal and a second distal end. Lumens extending from the proximal end to each of these distal ends provide for blood circulation within one or between two blood vessels. At least one aperture in one of the lumens positioned near the proximal end provides for active perfusion of blood to the patient's vasculature downstream of where the aperture resides in the vasculature when the catheter is inserted into the patient for treatment. The inventive catheter may comprise a third lumen positioned entirely within the patient's vasculature, providing passive perfusion of blood to the patient's vasculature downstream of where the third lumen resides in the vasculature when the catheter is inserted into the patient for treatment.

20 Claims, 4 Drawing Sheets

U.S. PATENT DOCUMENTS

| | | | | |
|---|---|---|---|---|
| 4,543,087 A | | 9/1985 | Sommercorn et al. | 604/43 |
| 4,692,141 A | | 9/1987 | Mahurkar | 604/43 |
| 4,944,745 A | * | 7/1990 | Sogard et al. | 606/194 |
| 4,976,270 A | | 12/1990 | Parl et al. | |
| 5,087,247 A | * | 2/1992 | Horn et al. | 604/98 |
| 5,129,883 A | | 7/1992 | Black | |
| 5,318,518 A | | 6/1994 | Plechinger et al. | 604/43 |
| 5,378,230 A | | 1/1995 | Mahurkar | 604/43 |
| 5,403,291 A | | 4/1995 | Abrahamson | 604/280 |
| 5,472,417 A | | 12/1995 | Martin et al. | 604/43 |
| 5,486,159 A | | 1/1996 | Mahurkar | 604/4 |
| 5,522,800 A | * | 6/1996 | Crocker | 604/96 |
| 5,542,937 A | | 8/1996 | Chee et al. | 604/280 |
| 5,554,136 A | | 9/1996 | Luther | 604/264 |
| 5,556,390 A | | 9/1996 | Hicks | 604/280 |
| 5,571,093 A | | 11/1996 | Cruz et al. | 604/270 |
| 5,776,111 A | | 7/1998 | Tesio | 604/264 |
| 5,785,686 A | * | 7/1998 | Runge | 604/96.01 |
| 5,795,326 A | | 8/1998 | Siman | 604/43 |
| 5,807,311 A | | 9/1998 | Palestrant | |
| 5,868,703 A | | 2/1999 | Bertolero et al. | |
| 5,947,953 A | * | 9/1999 | Ash et al. | 604/508 |
| 5,961,486 A | | 10/1999 | Twardowski et al. | 604/43 |
| 6,044,845 A | * | 4/2000 | Lewis | 128/898 |
| 6,059,760 A | * | 5/2000 | Sandmore et al. | 604/264 |
| 6,083,198 A | * | 7/2000 | Afzal | 604/101.01 |
| 6,200,260 B1 | | 3/2001 | Bolling | |
| 6,299,575 B1 | | 10/2001 | Bolling | |
| 6,371,935 B1 | * | 4/2002 | Macoviak et al. | 604/43 |
| 6,387,037 B1 | | 5/2002 | Bolling et al. | |
| 6,390,969 B1 | * | 5/2002 | Bolling et al. | 600/16 |
| 6,428,464 B1 | | 8/2002 | Bolling | |
| 6,488,662 B1 | | 12/2002 | Sirimanne | |
| 6,558,356 B1 | | 5/2003 | Barbut | |
| 6,610,004 B1 | | 8/2003 | Viole et al. | |
| 6,685,621 B1 | | 2/2004 | Bolling et al. | |
| 6,719,749 B1 | * | 4/2004 | Schweikert et al. | 604/544 |
| 2002/0111577 A1 | | 8/2002 | Sirimanne | |
| 2002/0169413 A1 | | 11/2002 | Keren et al. | |
| 2002/0188167 A1 | | 12/2002 | Viole et al. | |
| 2003/0069468 A1 | | 4/2003 | Bolling | |
| 2003/0083617 A1 | | 5/2003 | St. Germain et al. | |
| 2003/0144628 A1 | | 7/2003 | Sirimanne | |

* cited by examiner

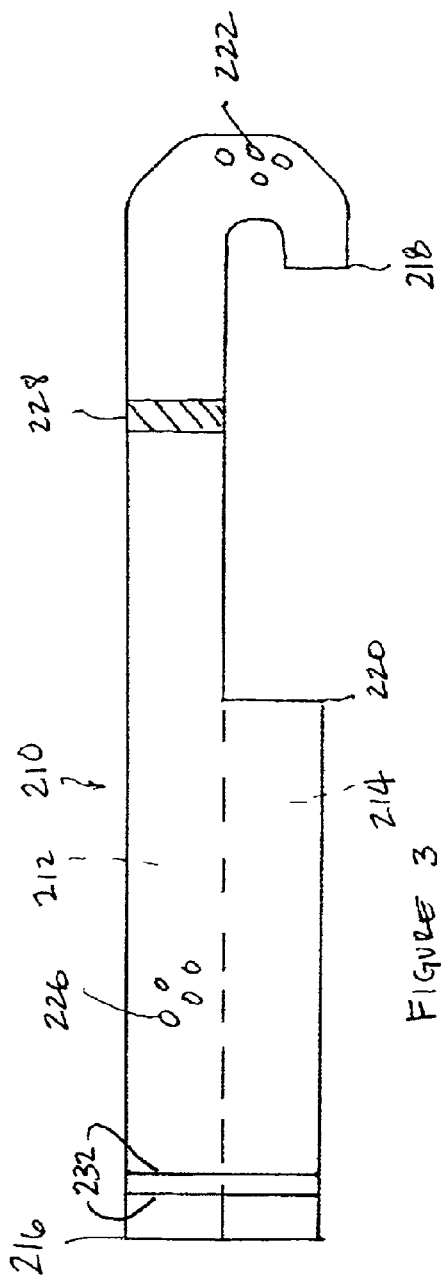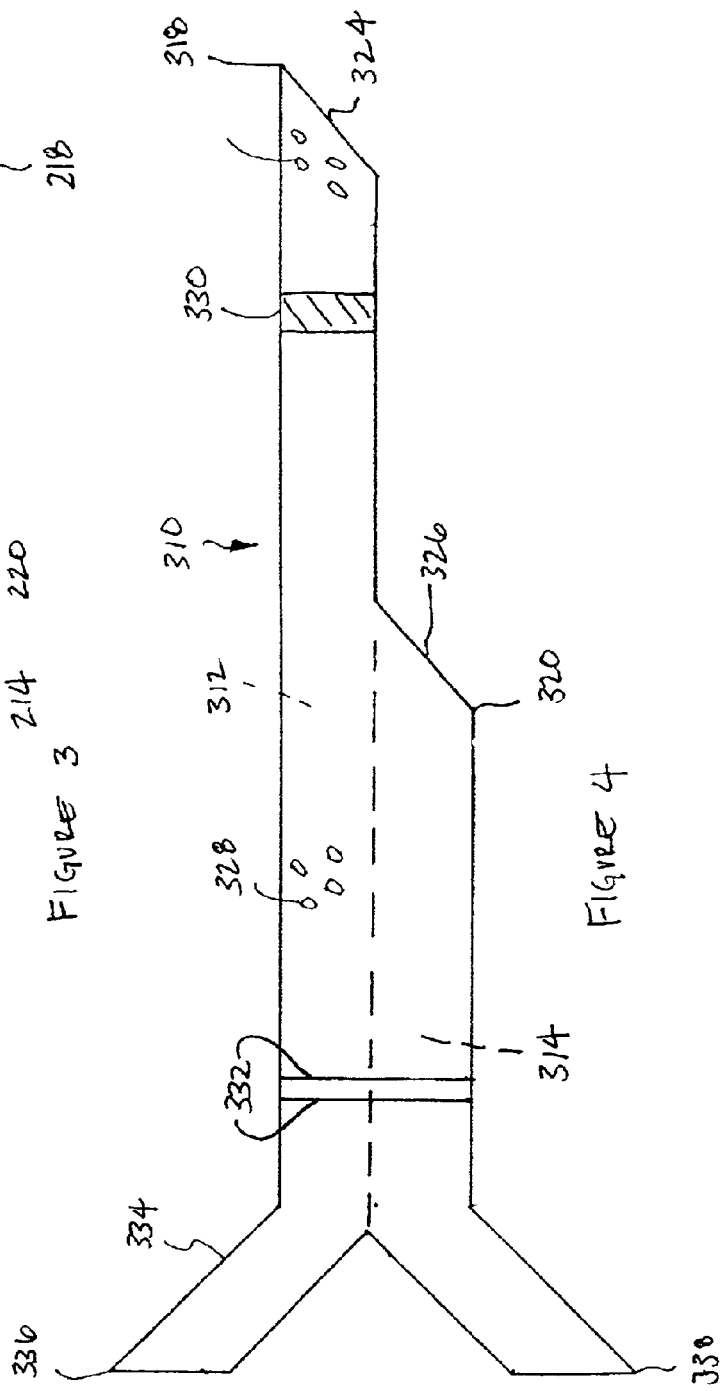

MULTILUMEN CATHETER FOR MINIMIZING LIMB ISCHEMIA

BACKGROUND OF THE INVENTION

1. Field of the Invention

The present invention relates to a multilumen catheter and, in particular, to multilumen catheters designed to prevent ischemia in patients when the catheter is positioned within the body.

2. Description of the Related Art

It is often necessary to divert the flow of blood from a patient's blood vessel back to the same or a different blood vessel as part of treating a patient suffering from one or more of numerous health impairments, including cardiovascular disease, such as congestive heart failure. Although surgical cut-down procedures can achieve this, percutaneous insertion of catheters has made this procedure less invasive and therefore less traumatic to the patient. Still, insertion of a cannula into the circulatory system can cause complex, and sometimes adverse, reactions within the body.

Some of the percutaneous procedures involve removing blood from the body and subsequently returning it to the body. For example, dialysis treatment involves first removing blood from the patient's circulatory system, treating the blood outside of the body, and then returning the blood to the patient's circulatory system to perfuse the various tissues and organs. Depending on the volume of blood flow, cannulae with large carrying capacity may be necessary. By maximizing the cross-sectional area of the cannula, the volume of blood that may be removed and/or returned to the patient's vascular system via the cannula is maximized. One approach to maximize the cross-sectional area of the cannula involves using either two single lumen catheters or a multilumen catheter. In a recirculation application, one lumen would function to withdraw blood and one would function to return blood to the patient. One problem with using two single lumen catheters is that it subjects the patient to multiple percutaneous insertion procedures, which complicates the procedure and increases the potential for infection and other complications. Therefore, it would be desirable to have a catheter assembly which could be inserted into the patient through a single insertion site.

Multilumen catheters in various forms have been employed for this purpose. For example, multilumen catheters have been made with two, three or more lumens to serve various aspiration and infusion functions, including extracting and returning blood to vessels, taking blood samples for testing and providing medications to the patient's vascular system. Simple multilumen catheters have been made by providing two round catheters of equal or nearly equal length joined by a web, or thin strip. This approach is described in U.S. Pat. No. 5,776,111 to Tesio. Other multilumen catheter designs have a unitary body with at least one septum dividing the lumens which extend from a proximal to a distal end.

While multilumen catheters require only a single puncture of the epidermis, their performance is limited in at least two ways. For one, the outer perimeter of the multilumen catheter cannot exceed the inner diameter of the vessel into which it is inserted. Furthermore, the already limited cross-sectional area must be divided into at least two lumens, one for withdrawal and one for return. Thus the carrying capacity of each lumen is further reduced. To supply the same amount of blood, the velocity and pressure of the blood in the lumens must increase over what it would be in the vessel itself. This has the potential to cause damage to the vessel as blood comes jetting out of the return lumen. Also, it may put further stress upon blood cells, even causing hemolysis. Thus, multilumen catheters must be made as large as possible to carry enough blood at satisfactory conditions.

Where the size of a catheter approaches the interior size of a vessel, less and less blood can flow around the catheter. As a result, limited blood supply reaches tissues and organs located downstream of the catheter in the vascular system. With insufficient perfusion, the tissues downstream of the lumen insertion site suffer from ischemia and become oxygen deprived. Prolonged oxygen deprivation can lead to tissue damage, as is well known in the art. Therefore, it would be desirable to have a multilumen catheter that can maximize cross-sectional area of withdrawal and return lumens while at the same time providing for acceptable levels of blood perfusion of tissue downstream of the catheter insertion site in the vascular system. It would also be advantageous to have a multilumen catheter that can also remove blood from one peripheral vessel and return blood to a second peripheral vessel.

SUMMARY OF THE INVENTION

Overcoming many if not all of the limitations of the prior art, the present invention comprises a multilumen catheter for directing the flow of blood to and from a patient through a single cannulation site. The catheter comprises a proximal end, a first distal end and a second distal end. The first distal end extends further from the proximal end than the second distal end. A first lumen extends between the first distal end and the proximal end and a second lumen extends between the second distal end and the proximal end. At least one aperture, but preferably a plurality of apertures may be formed in one of the first or second lumens positioned near the proximal end so that the aperture permits active maintenance or enhancement of perfusion of blood to the patient's vasculature downstream of where the aperture resides in the vasculature when the catheter is inserted into the patient for treatment. In an alternative embodiment, the multilumen catheter further comprises a third lumen with distal and proximal ends configured to be positioned entirely within the patient's vascular system. This third lumen is configured to permit the passive flow of blood downstream of the catheter site to maintain or enhance perfusion.

In one embodiment, a connector formed in the shape of a Y ("Y-connector") is positioned at the proximal end of the multilumen catheter. One leg of the Y-connector is in fluid communication with the first lumen and the other leg of the Y-connector is in fluid communication with the second lumen.

Preferably, in an application of the present invention, an outflow conduit of a pumping system is fluidly engaged to one lumen of the multilumen catheter and an inflow conduit of the same system is fluidly engaged to the other lumen. The inflow and outflow conduits are fluidly coupled to a pump so that, when connected to the patient, the pump circulates blood from one distal end of the multilumen catheter to the other distal end, and also through at least one aperture in one of the first or second lumens positioned near the proximal end. In one application, the multilumen catheter of the present invention is incorporated into an extracardiac pumping system for supplementing blood circulation in a patient without any component thereof being connected to the patient's heart. Such a system is described in U.S. Pat. No. 6,200,260, which is incorporated herein by reference. The system includes, in addition to the multilumen catheter, a pump configured to pump blood through the patient at subcardiac rates, an inflow conduit fluidly coupled to the pump to divert blood to the pump from a first blood vessel, and an outflow conduit fluidly coupled to the pump to direct blood from the pump to a second blood vessel.

The present invention also provides a method for treating a patient using the multilumen catheter of the present invention. The method comprises the step of inserting the multilumen catheter described above into the patient at a single cannulation site of a first blood vessel, locating the catheter such that a first lumen may be in fluid communication with a second blood vessel and a second lumen may be in fluid communication with the first blood vessel, withdrawing blood from one of said blood vessels through one of the first or said second lumens, and delivering blood through the other of said first or second lumens so that blood is delivered upstream and downstream of the cannulation site.

BRIEF DESCRIPTION OF THE DRAWINGS

These and other features and advantages of the invention will now be described with reference to the drawings, which are intended to illustrate and not to limit the invention.

FIG. 3 is a schematic of an alternative embodiment of the present invention multilumen catheter with a distal end comprising a J-tip configuration.

FIG. 4 is a schematic of an alternative embodiment of the present invention multilumen catheter comprising a Y-connector.

DETAILED DESCRIPTION OF THE PREFERRED EMBODIMENT

Turning now to the drawings provided herein, a more detailed description of the embodiments of the present invention is provided below.

Figure 1:
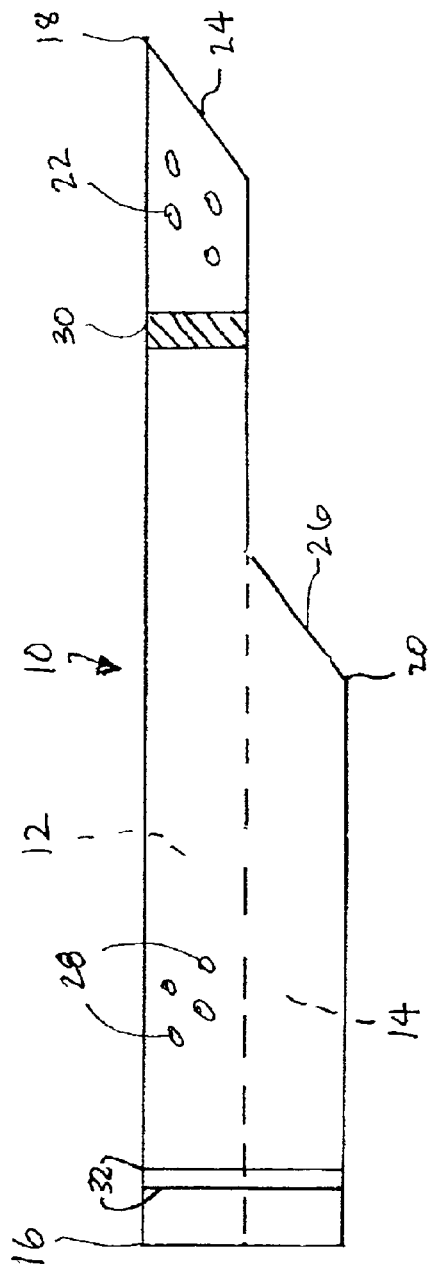
FIG. 1 is a schematic of one embodiment of the present invention multilumen catheter.

With reference to FIG. 1, one embodiment of the present invention comprises a multilumen catheter 10 designed to lessen ischemia that can occur when a large diameter catheter is inserted into a patient's blood vessel. The multilumen catheter preferably is of unitary construction and requires only one entry point into the patient's body. The multilumen catheter 10 comprises at least two lumens: a first lumen 12 and a second lumen 14. The first lumen 12 extends from a proximal end 16 of the multilumen catheter 10 to a first distal end 18. The second lumen 14 extends from the proximal end 16 of the multilumen catheter 10 to a second distal end 20. The lumens 12, 14 of the multilumen catheter 10 may be arranged one of many different ways. For example, the two lumens may be joined in a side-by-side manner, forming a "figure-8" when viewed from the proximal end 16. Alternately, a single cylindrical catheter housing may contain within it two or more side-by-side lumens. A cylindrical catheter housing could be formed with a diametral septum, i.e. a wall, extending across the cylinder at a diameter. A cylindrical housing with concentrically positioned lumens is also contemplated.

The first distal end 18 may be formed with one or more distal apertures 22, although such apertures may also be located in the second distal end 20. The distal apertures 22 may be positioned close together or spaced circumferentially around the distal end. The apertures 22 serve to decrease the pressure drop across the cannula tip, thereby minimizing damage to vessel walls from jetting effects. It may also be appropriate to practice methods for directing blood flow so as to minimize damage to vessel walls from jetting effects and from the recoil effect on the catheter of blood exiting a catheter. The present invention may further comprise a tapered tip 24 at the first distal end 18, which facilitates insertion and threading of the catheter into the patient. The present invention may also further comprise a tapered tip 26 at the second distal end 20.

One preferred embodiment of the multilumen catheter further comprises a set of apertures 28 positioned on the catheter 10 near the proximal end 16. The apertures 28 are formed on at least one lumen of the catheter to provide for fluid communication between one of the lumens 12, or 14 of the multilumen catheter 10 and the blood vessel in which it resides. A radiopaque marker 30 may be positioned at the distal end 18 of the multilumen catheter 10. The multilumen catheter could further comprise markings 32 near the proximal end of the multilumen catheter which are a known distance from one or more of the distal ends. These markings 32, as well as the marker 30 can be used to accurately position the catheter when applied to the patient.

Figure 2:
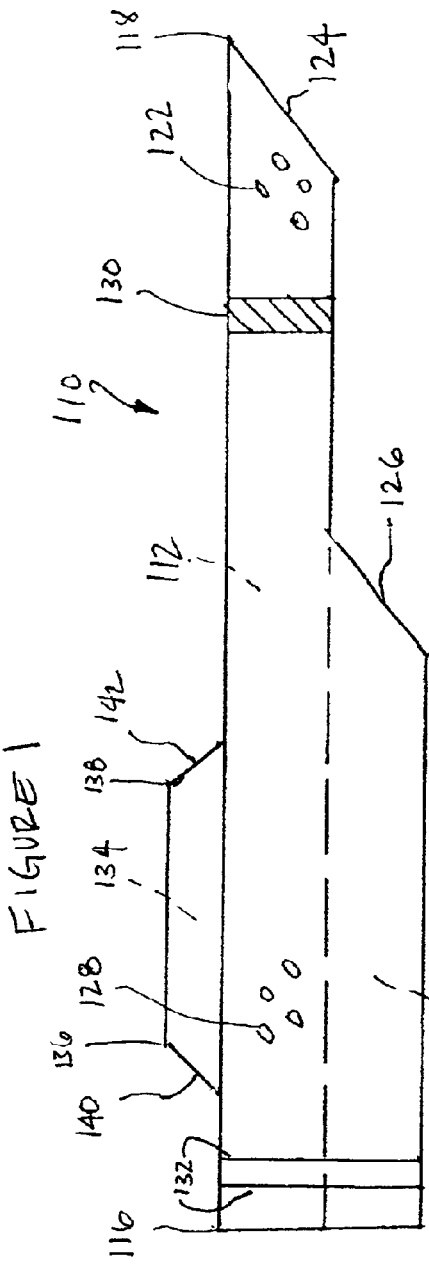
FIG. 2 is a schematic of an alternative embodiment of the present invention multilumen catheter.

In another embodiment of the present multilumen catheter shown in FIG. 2, the multilumen catheter 110 comprises a third lumen 134 extending between a proximal end 136 and a distal end 138. The lumen 134 is positioned and sized such that when the multilumen catheter 110 is applied to the patient (described below), the lumen resides entirely within the patient's body. As described above, the lumen 134 may be connected to the catheter 110 in a variety of ways. The purpose of the third lumen 134 is configured to permit the passive flow of blood downstream to the catheter to enhance perfusion. The embodiment shown in FIG. 2 also may have apertures 128 disposed near the proximal end 116 of the multilumen catheter 110. As described above, this embodiment may further comprise a tapered tip 140 at the distal end of the third lumen 134 and a tapered tip 142 at the proximal end of the third lumen 134 to facilitate application of the catheter to the patient.

In one variation of the three lumen embodiment the third lumen 134 may be made of collapsible material. In the collapsed state, the third lumen 134 would conform to at least a portion of the outside surface of the multilumen catheter 110. Once applied to the patient, as described in more detail below, the lumen 134 would be expanded to the deployed state shown in FIG. 2. This collapsible lumen could comprise a stone basket, or a frame similar to a stent. A stone basket is a structure that can be deployed within a patient's body and is used to capture objects. Here, the basket is used primarily to create a space between the catheter 110 and the vessel wall to permit the passive flow of blood downstream of the catheter site to enhance perfusion.

In an alternate embodiment of the multilumen catheter 210, shown in FIG. 3, the first distal end 218 is formed in the shape of a J-tip. That is, the opening at the distal end 218 may be curved such that blood exiting the lumen 212 is directed back along the multilumen catheter 210. Distal aperture(s) 222 may be formed at the bend of the J-tip so that blood also exits the lumen 212 and flows distal of the catheter 210. The "J" shape of the multi-lumen catheter tip may be formed and/or maintained by pre-loading it with a coil or with wire reinforcement, or by using a shape-memory material to create and maintain this shape. If the catheter is inserted so that the tip is straight and the "J" shape is deployed after the catheter inserted into the patient, the catheter may comprise a tapered tip at the first distal end 218, as described above.

Referring to FIG. 4, yet another alternative embodiment of the present invention multilumen catheter 310 comprises a Y-connector 334 formed at the proximal end of the multilumen catheter 310. As described above, the lumens are separated in any suitable way such that fluid communication is provided between the distal end 318 of the lumen 312 of the multilumen catheter 310 and the proximal end 336 of one leg of the Y-connector 334, and fluid communication is provided between the distal end 320 of the lumen 314 of the catheter 310 and the proximal end 338 of one leg of the Y-connector 334.

Any of the multilumen catheters described herein may be made from various materials to improve their viability in long-term treatment applications. For example, it is preferred that the biocompatibility of the catheter be improved compared to uncoated catheters to prevent adverse reactions such as compliment activation and the like. To prevent such side effects, the interior lumens of the catheters can be coated with biocompatible materials. Also known in the art are anti-bacterial coatings. Such coatings may be very useful on the outer surface of the catheter. This is especially true at or about where the catheter enters the patient's skin. At such a location, the patient is vulnerable to introduction of bacteria into the body cavity. Anti-bacterial coatings can reduce the likelihood of infection and thus improve the viability of long-term treatments.

Figure 5:
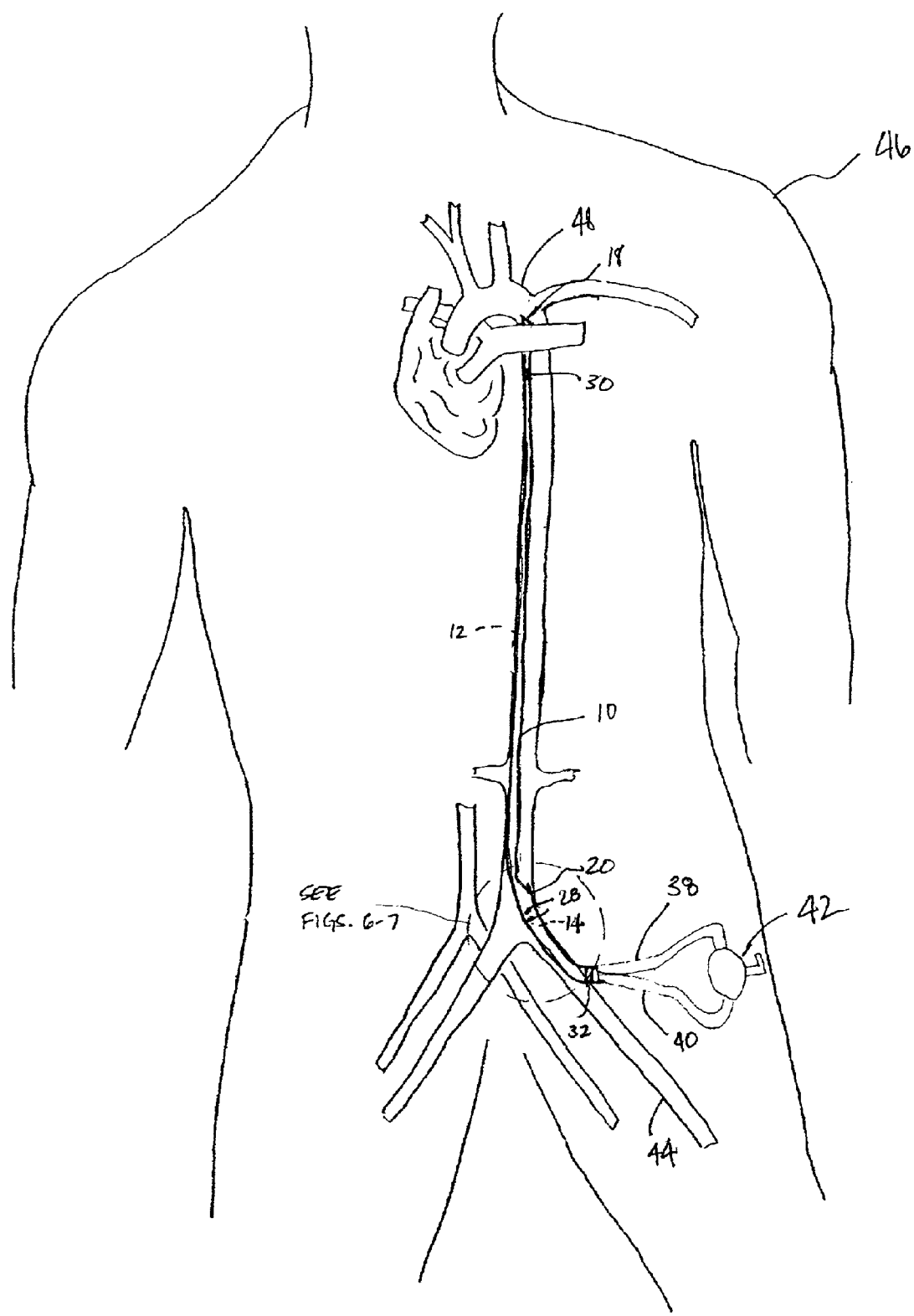
FIG. 5 is a schematic of one application of one embodiment of the multilumen catheter to a patient.

In one application, the multilumen catheter of the present invention may be integrated into a pumping system, such as the one described in more detail in U.S. Pat. No. 6,200,260. Referring to FIG. 5, such a system comprises the multilumen catheter 10, an inflow conduit 38, an outflow conduit 40 and a pump 42. One end of the outflow conduit 40 may be connected to the proximal end of the lumen 12, while the other end is connected to the inlet of the pump 42. One end of the inflow conduit 38 may be connected to the proximal end of the lumen 14, while the other end is connected to the outlet of the pump 42. This results in a flow from the first distal end 18 to the second distal end 20. Of course, the flow direction may be reversed using the same multilumen catheter, resulting in a flow from distal end 20 to distal end 18. In that case, the outflow conduit 40 is connected to the proximal end of lumen 14 and the inflow conduit 38 is connected to the proximal end of lumen 12. Referring to FIG. 5, the present multilumen catheter 10 when incorporated into a pumping system may be applied to a patient in an arterial-arterial fashion. Where the multilumen catheter 10 is inserted into the femoral artery 44 of the patient 46. The radiopaque marker 30 which may be incorporated into the distal end 18 of the multilumen catheter is used to track the insertion of the catheter so that to catheter may be positioned at a desired site within the patient's vascular system. As mentioned above, markings 32 on the proximal end could also be used to locate the distal end or ends.

In one example, the distal end 18 may be located in the aortic arch 48. The pump draws blood from the patient's vascular system in the area near the distal end 18 and into the lumen 12. This blood is further drawn into the conduit 40 and into the pump 42. The pump 42 then expels the blood into the lumen of the outflow conduit 38. This lumen carries the blood into the lumen 14 of the multilumen catheter 10 and back into the patient's vascular system in the area near the distal end 20. As described in greater detail below regarding FIGS. 6 and 7, the apertures 28 and/or the third lumen 134 provide blood flow to the patient's vasculature downstream of where the multilumen catheter resides in the vasculature to maintain or enhance perfusion of blood. The blood flow in the multilumen catheter may be reversed. In that case, blood is drawn from the patient through distal end 20 and returned to the patient through distal end 18.

Figure 6:
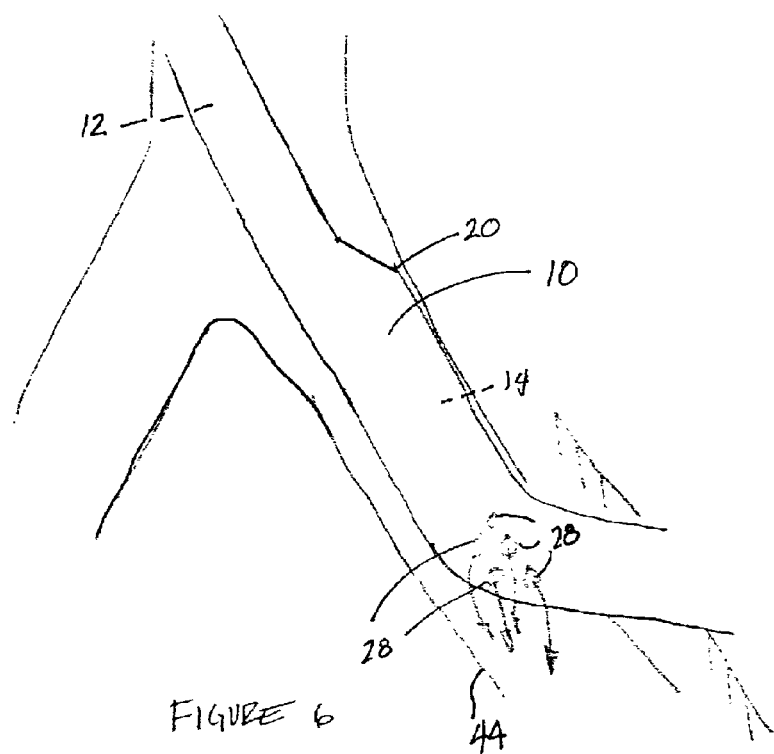
FIG. 6 is an enlarged view of a portion the proximal end of the embodiment shown in FIG. 1 applied to a patient.

Referring to FIG. 6, the multilumen catheter 10 comprises features that will maintain or increase the blood flow to downstream tissue when the catheter is inserted into the patient. The apertures 28 provide for fluid communication between at least one lumen 12 or 14 and the patient's blood vessel. The apertures 28, thus, provides active perfusion of the downstream tissues.

Figure 7:
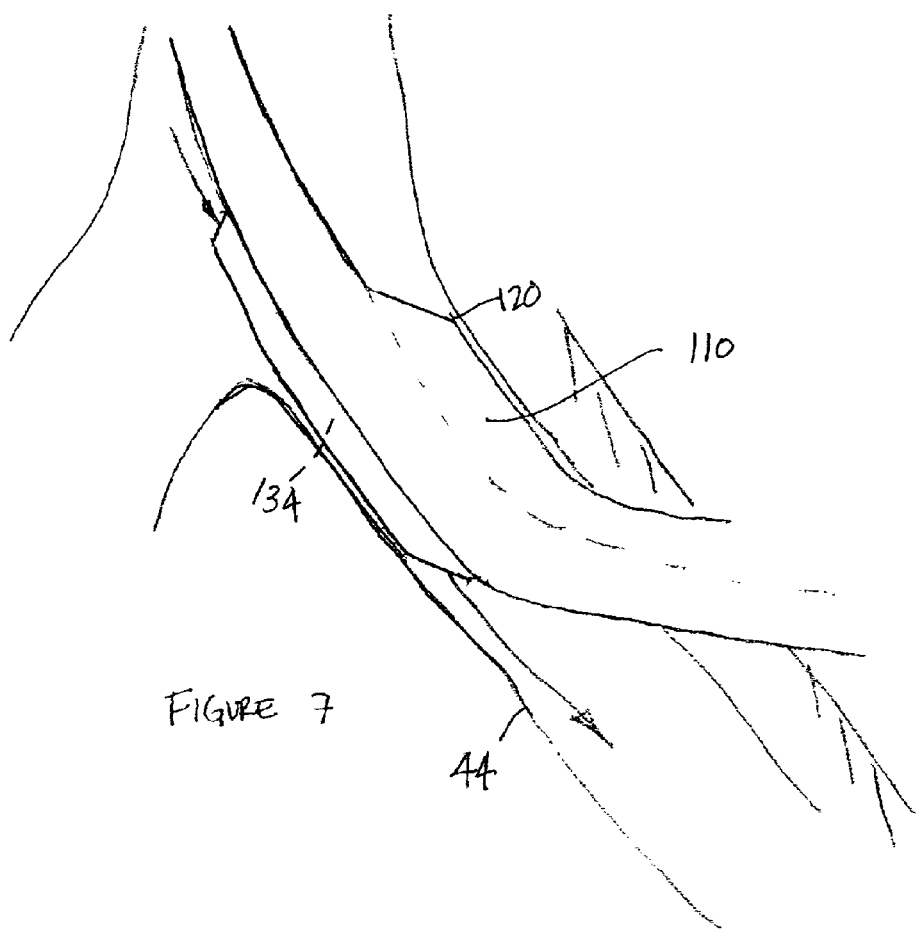
FIG. 7 is an enlarged view of a portion the proximal end of the embodiment shown in FIG. 2 applied to a patient.

Referring to FIG. 7, the lumen 134 of the embodiment shown in FIG. 2 is located entirely within the vessel when the catheter 110 is inserted into the patient. The lumen provides a pathway for blood flow to tissue downstream of the catheter so that the catheter 110 may maintain or increase the flow of blood to downstream tissue. The lumen 134, thus, provides passive perfusion. If desired, apertures may be included in one of the other two lumens to supplement passive perfusion with active perfusion.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A multilumen catheter for directing the flow of blood through a patient through a single cannulation site, said catheter comprising:

a catheter body having a proximal end configured to enable the catheter to be applied through a single cannulation site, a first distal end, and a second distal end, said first distal end extending distally further from the proximal end than the second distal end and said second distal end being closer to the proximal end than to the first distal end;

a first lumen at least partially defined by a wall for passing blood through the body extending between said first distal end and said proximal end adapted to fluidly communicate with the patient;

a second lumen at least partially defined by the wall for passing blood through the body extending between said second distal end and said proximal end adapted to fluidly communicate with the body independently of the first lumen; and at least one aperture on said body communicating with said first lumen, wherein the distance from the first distal end to the aperture is a first length, the distance from the second distal end to the aperture is a second length, and the distance from the first distal end to the second distal end is a third length, wherein the first length is greater than the third length and the first length is at least three times greater than the second length;

said catheter body having a continuous outer surface surrounding said first and said second lumens along at least a portion of said body distal of said aperture;

wherein at a location where the distance between the first and second lumens is smallest, only a single wall extends between the first and second lumens at least at the second distal end.

2. The multilumen catheter of claim 1 further comprising a Y-connector positioned at the proximal end, wherein a first leg of the Y-connector is in fluid communication with said first lumen and a second leg of the Y-connector is in fluid communication with said second lumen.

3. The multilumen catheter of claim 1 further comprising an outflow conduit fluidly engaged to one lumen and an inflow conduit fluidly engaged to the other lumen, said inflow and outflow conduits fluidly coupled to a pump so that when connected to a patient, said pump circulates blood from one distal end of said multilumen catheter to the other distal end and also through the at least one aperture.

4. The multilumen catheter of claim 3 wherein one of said distal ends comprises at least one distal aperture.

5. The multilumen catheter of claim 3 further comprising a third lumen having a distal and a proximal end configured to be positioned entirely within the patient's vascular system.

6. The multilumen catheter of claim 1 wherein the first distal end is tapered.

7. The multilumen catheter of claim 1 wherein the second distal end is tapered.

8. The multilumen catheter of claim 1 wherein one of said distal ends comprises at least one distal aperture.

9. The multilumen catheter of claim 1 wherein said first distal end comprises a J-tip comprising a bend.

10. The multilumen catheter of claim 9 wherein said J-tip comprises an aperture positioned at the distal-most portion of the bend.

11. The multilumen catheter of claim 1 further comprising a radiopaque marker, wherein the radiopaque marker can be used to position the catheter when the catheter is applied to a patient.

12. The multilumen catheter of claim 1 further comprising an indicator near the proximal end, wherein the indicator can be used to position the catheter when the catheter is applied to a patient.

13. The multilumen catheter of claim 1 further comprising a third lumen having a distal and a proximal end configured to be positioned entirely within the patient's vascular system.

14. The multilumen catheter of claim 13 wherein the distal end of the third lumen is tapered.

15. The multilumen catheter of claim 14 wherein the proximal end of the third lumen is tapered.

16. An extracardiac pumping system for supplementing blood circulation in a patient without any component thereof being connected to the patient's heart, the extracardiac system comprising:
   a pump configured to pump blood through the patient at subcardiac flow rates, said pump having an average flow rate that, during normal operation thereof, is substantially below that of the patient's heart when healthy;
   an inflow conduit fluidly coupled to the pump to direct blood to the pump from a first blood vessel;
   an outflow conduit fluidly coupled to the pump to direct blood from the pump to a second blood vessel; and
   a multilumen catheter for directing the flow of blood through a patient through a single cannulation site, said catheter comprising
   a catheter body having a proximal end, a first distal end, and a second distal end, said first distal end extending distally further from the proximal end than the second distal end;
   a first lumen extending between said first distal end and said proximal end, said first lumen in fluid communication with one of said conduits; and
   a second lumen extending between said second distal end and said proximal end, said second lumen in fluid communication with one of said conduits, wherein the pump is oriented to deliver fluid from the pump to the second lumen;
   wherein at a location where the distance between the first and second lumens is smallest, only a single wall extends between the first and second lumens at least at the second distal end.

17. The extracardiac pumping system of claim 16 further comprising at least one aperture in one of said lumens positioned near the proximal end so that the aperture may enhance perfusion of blood to the patient's vasculature downstream of where the aperture resides in said vasculature when said catheter is inserted into the patient for treatment.

18. The extracardiac pumping system of claim 16 wherein said first lumen is in fluid communication with said outflow conduit and said second lumen is in fluid communication with said inflow conduit.

19. The extracardiac pumping system of claim 16 wherein said first lumen is in fluid communication with said inflow conduit and said second lumen is in fluid communication with said outflow conduit.

20. A multilumen catheter for directing the flow of blood through a patient through a single cannulation site, said catheter comprising:
   a catheter body having a proximal end configured to enable the catheter to be applied through a single cannulation site, a first distal end, and a second distal end, said first distal end extending distally further from the proximal end than the second distal end and said second distal end being closer to the proximal end than to the first distal end;
   a first lumen at least partially defined by a wall for passing blood through the body extending between said first distal end and said proximal end adapted to fluidly communicate with the patient;
   a second lumen at least partially defined by the wall for passing blood through the body extending between said second distal end and said proximal end adapted to fluidly communicate with the body independently of the first lumen; and
   at least one aperture on said body communicating with said first lumen, wherein the distance from the first distal end to the aperture is a first length, the distance from the second distal end to the aperture is a second length, and the distance from the first distal end to the second distal end is a third length, wherein the first length is greater than the third length and the first length is at least three times greater than the second length;
   wherein at a location where the distance between the first and second lumens is smallest, only a single wall extends between the first and second lumens at least at the second distal end.

* * * * *

UNITED STATES PATENT AND TRADEMARK OFFICE
CERTIFICATE OF CORRECTION

| | | |
|---|---|---|
| PATENT NO. | : 7,048,680 B2 | Page 1 of 1 |
| APPLICATION NO. | : 09/876281 | |
| DATED | : May 23, 2006 | |
| INVENTOR(S) | : Anthony Viole et al. | |

It is certified that error appears in the above-identified patent and that said Letters Patent is hereby corrected as shown below:

At Column 3, Line 43, Delete "EMBODIMENT" and insert --EMBODIMENTS --

Signed and Sealed this

Thirteenth Day of March, 2007

JON W. DUDAS
*Director of the United States Patent and Trademark Office*